United States Patent [19]

Ferrero et al.

[11] Patent Number: 5,431,918
[45] Date of Patent: Jul. 11, 1995

[54] BREATH MINT CONFIGURATION

[75] Inventors: Pietro Ferrero, Waterloo, Belgium; Tomaso Damonte, Alba, Italy

[73] Assignee: Soremartec S.A., Arlon-Schoppach, Belgium

[21] Appl. No.: 968,683

[22] Filed: Oct. 30, 1992

[51] Int. Cl.⁶ ............................................... A61K 7/16
[52] U.S. Cl. ...................................... 424/464; 424/440
[58] Field of Search .............................. 424/464, 440

[56] References Cited

U.S. PATENT DOCUMENTS

| | | | |
|---|---|---|---|
| D. 54,074 | 11/1919 | Fritz | D1/127 |
| D. 269,721 | 7/1983 | Tovey | D28/01 |
| 701,438 | 6/1902 | Whyte | 368/313 |
| 2,304,246 | 12/1942 | Ekert | 99/135 |
| 2,687,367 | 8/1954 | Burrin | 167/82 |
| 4,409,202 | 10/1983 | Witzel et al. | 424/440 |
| 4,493,822 | 1/1985 | Tovey . | |
| 4,569,852 | 2/1986 | Yang | 426/534 |
| 4,693,886 | 9/1987 | Ayer . | |
| 4,735,805 | 4/1988 | Ni et al. . | |
| 5,116,619 | 5/1992 | Greco et al. . | |
| 5,284,659 | 2/1994 | Cherukuri et al. | 424/441 |

OTHER PUBLICATIONS

Schmidt, Nicholas F., et al. "The Correlation between Organoleptic Mouth–Odor Ratings and Levels of Volatile Sulfur Compounds", *Oral Surgery Oral Med. Oral Pathol.*, vol. 45, pp. 560–567 (1978).

Primary Examiner—Thurman K. Page
Assistant Examiner—Amy Hulina
Attorney, Agent, or Firm—Rothwell, Figg, Ernst & Kurz

[57] ABSTRACT

A breath mint tablet with improved breath freshening efficacy has a tablet body with oblong front and back face portions having opposing ends connected by substantially parallel sides. The tablet is substantially elliptical when viewed end on, and has a thickness dimension front-to-back, a width dimension side-to-side, and a length dimension end-to-end. The length and width dimensions have a ratio in the range of about 1.28:1 to about 1.93:1 and the width and thickness dimensions have a ratio in the range of about 1.08:1 to about 2.25:1.

16 Claims, 9 Drawing Sheets

BREATH MINT CONFIGURATION

BACKGROUND OF THE INVENTION

1. Field of the Invention

The present invention relates to the field of tablet configurations, especially breath freshening tablets.

2. Description of the Background Art

Breath freshening tablets are popular items which typically are consumed by being dissolved in the mouth rather than by being chewed or swallowed whole. Such tablets are intended to freshen the breath of the user, and are primarily made up of sugar or sugar substitute, with other ingredients such as dextrin, starch, arabic gum, carnauba wax, magnesium stearate, natural and/or artificial flavors, and natural and/or artificial colors. The tablets can be flavored with, for example, various types of mint, such as peppermint, spearmint, wintergreen and the like, or can be fruit or spice flavored, such as orange or cinnamon. Regardless of the flavor, such tablets are typically and generically referred to as mints or breath mints. For the purpose of the disclosure herein "tablet," "mint" and "breath mint" are used interchangeably. A popular brand of breath mint is TIC TAC®, manufactured by the assignee of the present invention, Ferrero S.p.A. of Italy. Other brands of breath mints include BREATHSAVERS® and CERTS®. The CERTS breath mints are currently available in a "flat" disk form and a small bean shape having a "belt"-shaped ridge circumscribing its equatorial plane. Other shaped tablets of mints, candy, and medicinal products are disclosed in Design U.S. Pat. No. 54,074 to Fritz; U.S. Pat. No. 4,735,805 to Ni et al.; U.S. Pat. No. 2,304,246 to Ekert; U.S. Pat. No. 2,687,367 to Burrin; U.S. Pat. No. 701,438 to Whyte; U.S. Pat. No. 4,693,886 to Ayer; Design U.S. Pat. No. 269,721 to Tovey; and U.S. Pat. No. 4,493,822 to Tovey.

The TIC TAC® breath mint is particularly recognizable by its small oblong or bean-shaped configuration. This uniquely shaped mint has been quite popular as a breath freshening mint as it possesses effective breath freshening properties. For example, an efficacious mint is one which not only initially after being consumed imparts a fresh smell and sensation to the consumer's mouth, but one which also maintains the freshness over a period of time. A mint is typically more effective if it imparts a freshness that slowly dissipates over that period of time.

Several factors affect the efficacy of a mint. The mint's ability to uniformly distribute the mint flavor is one factor. Typically, the more uniform the distribution, the more efficacious the mint is in freshening breath or suppressing malodor. The flavor of the mint also influences the freshening capability of the mint. Stronger flavors such as cinnamon appear to be more efficacious. Taking these factors, as well as others, into consideration the breath mint art seeks to improve a mint's breath freshening efficacy, including a mint's breath freshening efficacy over extended periods of time.

SUMMARY OF THE INVENTION

A tablet with significantly improved breath freshening efficacy has been prepared by varying the "bean" shape of the TIC TAC® breath mint. The new and improved mint comprises a tablet body with oblong front and back face portions having opposing ends connected by substantially parallel sides. The opposing ends are preferably semi-circular. The tablet is substantially elliptical when viewed end-on, and has a thickness dimension front-to-back, a width dimension side-to-side, and a length dimension end-to-end. In accordance with the present invention, the length and width dimensions have a ratio in the range of about 1.28:1 to about 1.93:1 and the width and thickness dimensions have a ratio of about 1.08:1 to 2.25:1. Hereinafter, the shape of the new mint is described as a "pressed-bean." The pressed-bean results in significantly improved breath freshening properties for a variety of flavors. In particular, the new pressed-bean mint exhibits better breath freshening properties over extended periods of time than those exhibited by the prior art bean-shaped mint.

DETAILED DESCRIPTION OF THE PREFERRED EMBODIMENTS

Figure 1:
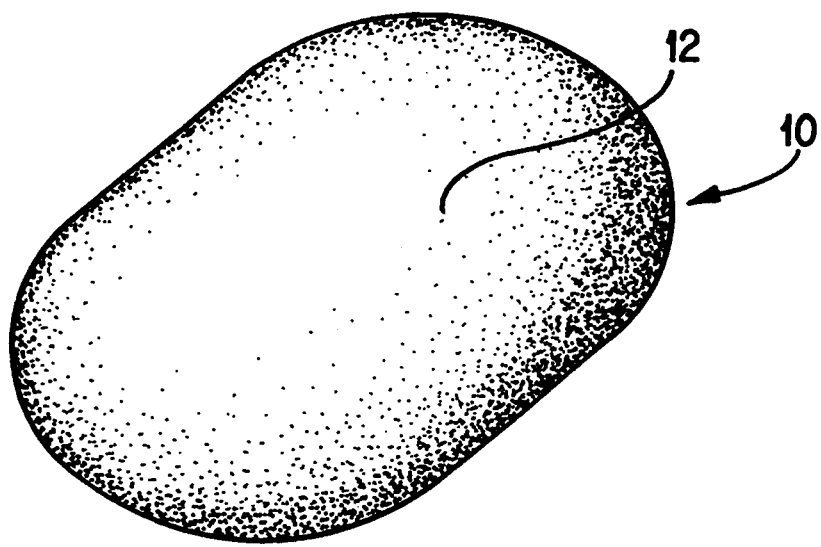
FIG. 1 is a perspective view of a tablet in accordance with the present invention.
Figure 1A:
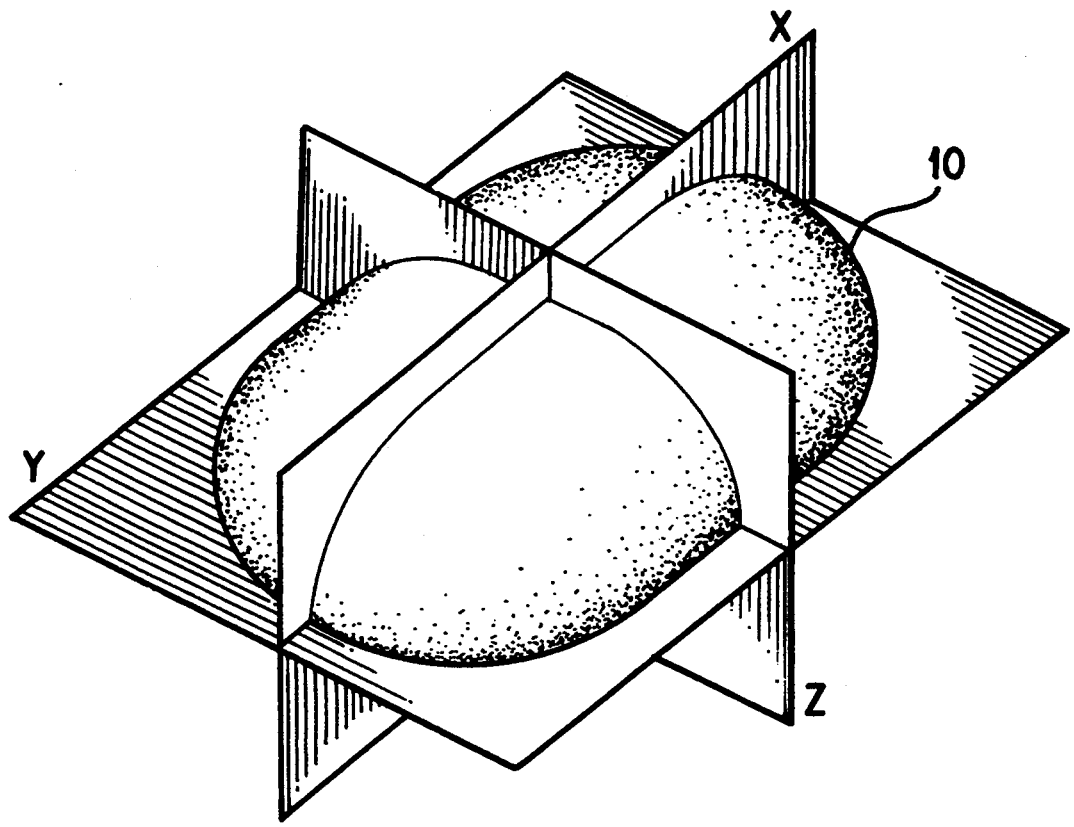
FIG. 1A is a view of FIG. 1 indicating the cross sectional views illustrated in FIGS. 2–4.
Figure 4:
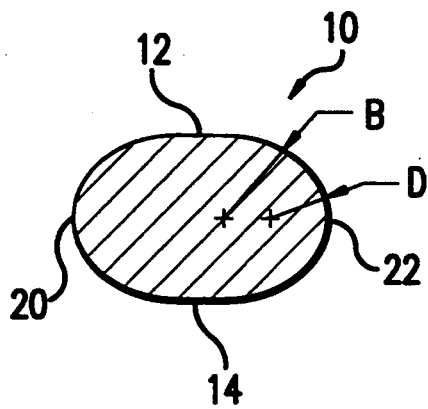
FIG. 4 is a vertical cross section through Z of the tablet of FIG. 1A.

FIG. 1 shows a tablet 10 which imparts improved breath freshening efficacy in accordance with the present invention. FIG. 1 illustrates a preferred configuration of the tablet, which, when viewed end-on as shown in FIG. 4, is substantially elliptical. The term "elliptical" has its conventional meaning, i.e., having a shape that is oval, or a shape that is a closed plane curve generated by a point moving in such a way that the sums of the curve's distances from two fixed points is a constant. See, for example, *Webster's New Collegiate Dictionary*, 1979.

Figure 2:
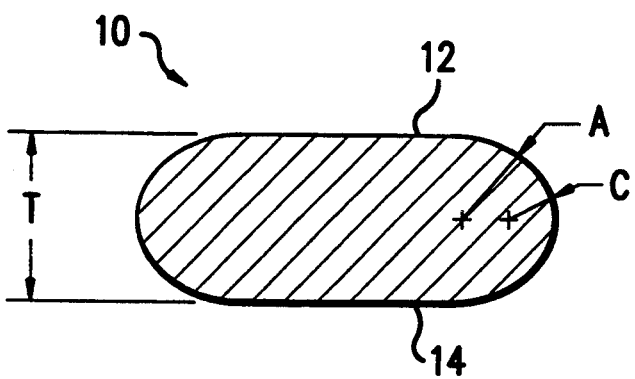
FIG. 2 is a tactical cross section through X of the tablet of FIG. 1A.

As can be seen in FIG. 2, preferred tablet 10 has oblong front and back portions 12 and 14, respectively, of the tablet's surface.

Figure 3:
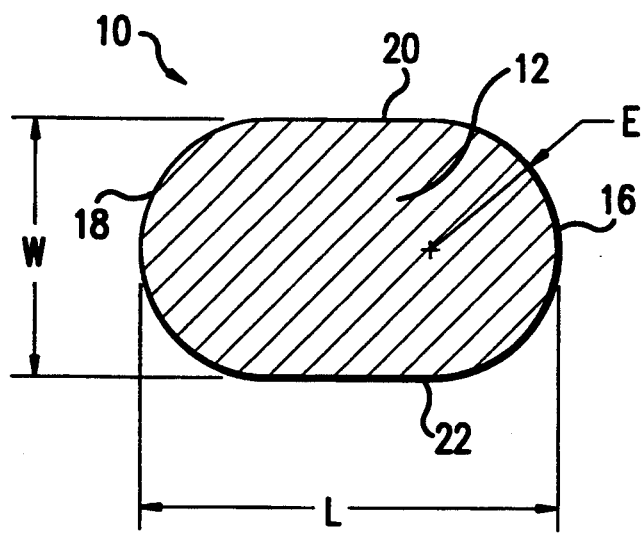
FIG. 3 is a horizontal cross section Y of the tablet of FIG. 1A.

FIG. 3 shows opposing semi-circular ends 16 and 18, connected by substantially parallel sides 20 and 22.

In accordance with the present invention, tablet body 10 has a thickness dimension T, as illustrated in FIG. 2, and a width dimension W and a length dimension L as illustrated in FIG. 3. Suitable ratios of L:W for tablets according to this invention are in the range of 1.28:1 to 1.93:1. Suitable ratios of W:T are in the range of about 1.08:1 to 2.25:1. Most preferred L:W and W:T ratios are about 1.58:1 and about 1.51:1, respectively.

Suitable thicknesses for the a tablet configuration having a weight in the range of about 0.25 to about 0.5 g are in the range of from about 4 mm to about 6.5 mm. A preferred thickness dimension is within the range of from about 4.5 mm to about 6.0 mm, more preferably, from about 5 mm to about 5.6 mm, even more preferably from about 5.1 mm to about 5.5 mm, still more preferably from about 5.2 mm to about 5.4 mm and most preferably about 5.3 mm.

The width dimension of the preferred configuration can be in the range of from about 7 mm to about 9 mm. The preferred width dimension is within the range of from about 7.5 mm to about 8.5 mm, more preferably from about 7.7 mm to about 8.3 mm, even more preferably from 7.8 mm to about 8.2 mm, still more preferably from about 7.9 mm to about 8.1 mm, and most preferably about 8 mm.

The length dimension of the preferred configuration is within the range of from about 11.5 mm to about 13.5 mm. Preferred length dimensions are within the range of from about 12 mm to about 13 mm, more preferably from about 12.3 mm to about 12.9 mm, even more preferably from about 12.4 mm to about 12.8 mm, still more preferably from about 12.5 mm to about 12.7 mm and most preferably about 12.6 mm.

The inventive tablet configurations are particularly suitable for breath mints which, as noted above, are primarily made up of sugar or sugar substitute, and may contain minor amounts of such other ingredients as dextrin, starch, arabic gum, carnauba wax, magnesium stearate, natural and/or artificial flavors, natural and/or artificial colors, and the like. The breath mints can be made utilizing any suitable tableting machine as is known in the art, but preferably are prepared by conventional pan-coating techniques. Such techniques comprise coating seed particles or cores with the appropriate ingredients and allowing the coating to accumulate to a desired thickness. In this invention, the coating is allowed to accumulate until tablets having the dimensions and weight described herein are obtained. In addition, the core is shaped to provide a tablet having the desired dimensions and weight described below.

Breath mint tablets in accordance with preferred configurations of the present invention can be made in various sizes and weights. As indicated above, one particular embodiment has a weight within the range of 0.25 g to 0.5 g, preferably within the range of 0.3 g to 0.45 g, more preferably with the range of 0.33 g to 0.43 g, even more preferably within the range of 0.34 g to 0.42 g, still more preferably within the range of 0.35 g to 0.41 g, and most preferably within the range of 0.36 g to 0.4 g.

In a larger embodiment the preferred weight range is 1.0 g to 2.0 g. As with the smaller embodiment, tablet dimensions can vary depending on the pan coating conditions employed in making the tablet. Suitable width, length and thickness dimensions for an embodiment having a weight of about 1.5 g are 11.65 mm, 18.80 mm and 7.10 mm, respectively. The radius of curvature R at E is a radius of curvature for the end of the tablet body and is equal to W/2. As with the tablet dimensions discussed above, the radius of curvatures depend on the pan coating conditions employed to prepare the tablet. The tablet, for example, has a radius of curvature R at A so that suitable dimensions for a tablet weighing 2.0 g can include width, length and thickness dimensions of 12.80, 20.70 and 7.80 mm, respectively.

Various sections of the tablet body have a radius of curvature as illustrated in FIGS. 2–4. Radius of curvature R at A and B is a radius of curvature of the end of tablet 10. Radius A is such that the ratio of A/T is in the range of about 1.20/1 to about 1.40/1. The radius of curvature R at B is such that B/T is in the range of 0.9/1 to about 1.1/1. The radius of curvatures R at C and D are equal and are such that the ratios of C/T and D/T are in the range of about 0.35/1 to about 0.45/1.

Figure 5:
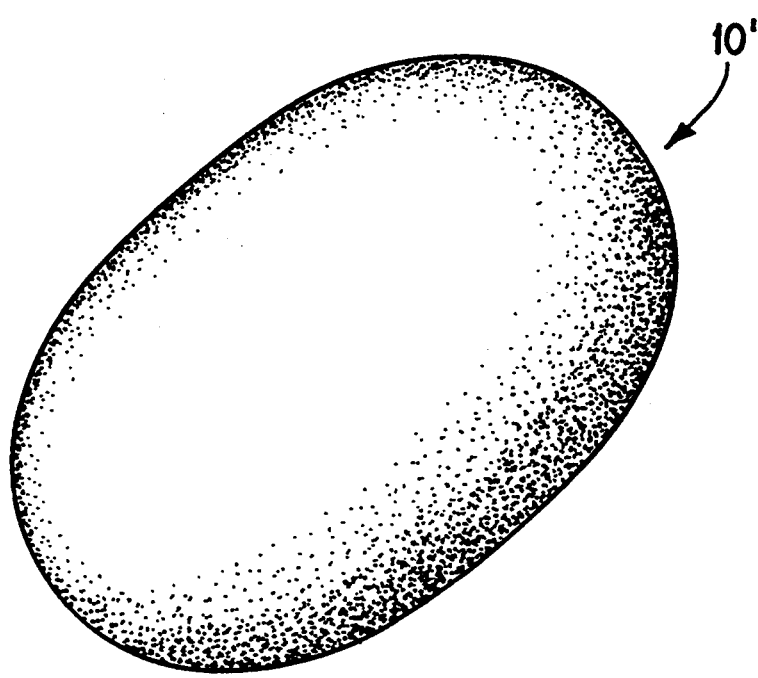
FIG. 5 is a perspective view of a prior art tablet.
Figure 6:
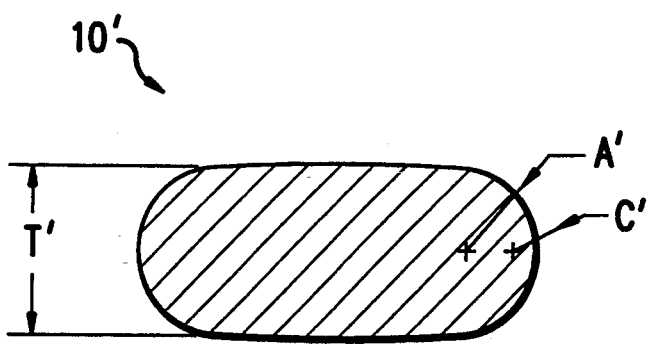
FIG. 6 is a side elevation view of the prior art tablet of FIG. 5.
Figure 7:
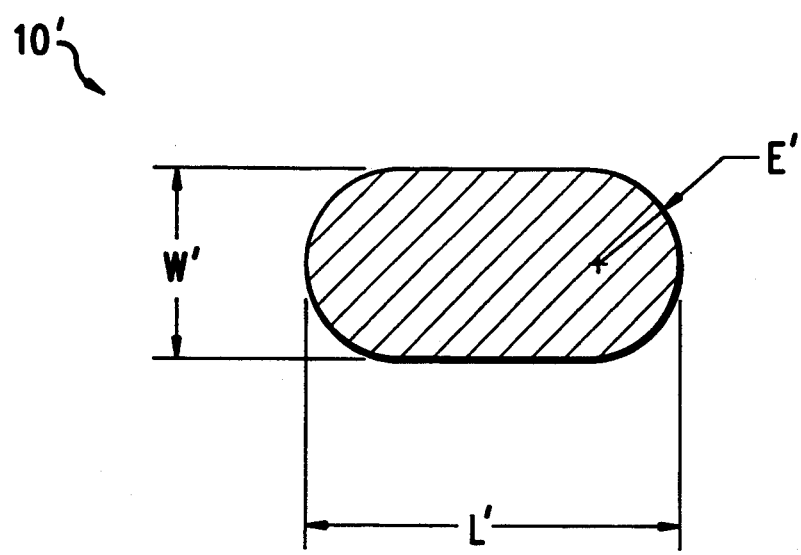
FIG. 7 is a top elevation view of the prior art tablet of FIG. 5.
Figure 8:
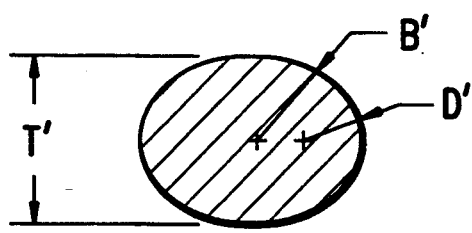
FIG. 8 is an end elevation view of the prior art tablet of FIG. 5.

FIG. 5 shows a prior art breath mint tablet body 10'. With reference to FIGS. 6 and 8, the prior art breath mint tablet body 10' has a thickness dimension T' of 5.6 mm. Referring to FIG. 7, the prior art breath mint tablet body 10' has a width dimension W' of 6.5 mm, and a length L' of 11.1 mm.

As shown in FIGS. 6 and 8, prior art tablet 10' has a radius of curvature R' at A' and B' of 6.5 mm and 5.0 mm, respectively, or A'/T' and B'/T' of 1.16 and 0.89, respectively. Tablet 10' has a radius of curvature R' at C' and D' of 2.0 mm or a C'/T' and D'/T' of 0.34. The radius of curvature of the tablet at E' in FIG. 7 is 3.65 mm.

As indicated earlier, breath mint tablets in accordance with the present invention as shown in FIGS. 1 to 4 show significant improvement in breath freshening efficacy over the prior art breath mint tablets shown in FIGS. 5 to 8. For instance, the pressed-bean mints according to this invention and the prior art bean-shaped mints initially show substantially similar reduction in mouth odor immediately after the mint was consumed. As time elapses, however, the pressed-bean unexpectedly exhibits a higher level of efficacy in breath freshening over the levels shown by the prior art mint. The following examples, which are provided as merely illustrative as opposed to limiting, illustrate this improved efficacy of the present invention.

EXAMPLES

To illustrate the improved breath freshening efficacy of the present invention, a comparative study between the prior art bean-shaped mint and the pressed-bean mint according to this invention was conducted. The study employed a methodology which is used and accepted by the National Association of Broadcasters (N.A.B.) and the television networks when reviewing the accuracy of advertisements which make superiority claims for breath freshening products. This methodology has thus been relied upon by those skilled in the art as a fair and accurate test of mints, mouth washes, etc. in terms of the products' breath freshening efficacy. Similar methodology is mentioned in Schmidt et al.'s "The Correlation Between Organoleptic Mouth-Odor Ratings and Levels of Volatile Sulfur Compounds", *Oral Surgery Oral Med. Oral Pathol.*, vol. 45, pp. 560–67 (1978).

The study was carried out using twenty test subjects and three judges. The test subjects were instructed to avoid any activity which might affect the test. Subjects were instructed to avoid highly seasoned foods on the day prior to the test, were instructed to not smoke from midnight of the day prior to the test until the test was complete, to avoid breakfast or coffee on the day of the test, to avoid use of mouthwashes or breath fresheners on the day of the test and no tooth brushing was permitted, no lipstick or other scented cosmetics were permitted on the subjects and no beverage was permitted during the test. The mints tested weighed 0.38 gm and have length, width, and thickness dimensions as discussed above. In addition, the radius of curvatures for the tablet were in the ranges discussed above.

The judges evaluated the breath odor of the test subjects in order to determine the efficacy of the mints tested. The breath of the subjects was first assigned an intensity value on a scale of 0 to 8, with 0 representing little breath odor and 8 representing the highest level of breath odor. The level of each subject's breath odor was evaluated before treatment, immediately after treatment (the time immediately after the mint had completely melted), and 15, 30, 60, 90, 120 and 180 minutes after treatment. The evaluation was carried out on two separate days, with the same twenty subjects in the study on both days. All subjects received only one of the products on each test day. The product evaluation sessions were also scheduled so that at least one day of rest was allowed between test days.

The results determined by the judges were then used to calculate the percentage reduction in breath odor due to treatment of each of the mints tested. The calculations used are indicated below:

$$\text{Percent Odor Reduction} = \frac{B_o - B_t}{B_o} \times 100$$

where:

$B_o$—The breath score before treatment
$B_t$—The breath score at the time of evaluation Thus, a totally effective treatment will yield a 100 percent odor reduction and a totally ineffective treatment will yield a zero percent reduction.

Using best fit statistical procedures, the data was then fitted onto a logarithmic curve of the following general form:

$$Y = Y_o 10^{-bt}$$

where:
Y=Percent malodor reduction
$Y_o$=Initial percent malodor reduction
b=Slope of curve
t=Time in hours In addition, several flavors of the pressed-bean mints and the prior art bean-shaped mints were tested. Using best fit statistical procedures, the percentage reduction data was fitted on logarithmic curves illustrated by FIGS. 9a-9e. The following tables indicate the test results generated according to this study for each respective flavor. The equations describing the best fit line for each sample are indicated in each example.

Example 1

| PERCENT MORNING BREATH MALODOR REDUCTION FRESHMINT PRIOR ART MINT VERSUS PRESSED-BEAN MINT | | |
|---|---|---|
| Time (hours) | Prior Art | Pressed-Bean |
| 0.0 | 96.4 | 93.9 |
| 0.25 | 86.7 | 85.4 |
| 0.5 | 83.5 | 84.7 |
| 1.0 | 69.2* (t = 4.39) | 78.6 |
| 1.5 | 64.9* (t = 3.94) | 72.4 |
| 2.0 | 57.8* (t = 3.40) | 65.3 |
| 3.0 | 50.4* (t = 5.97) | 63.7 |

*Significantly different from pressed-bean mint using t-test analysis at 99% and above confidence level.

The above data suggest a significant difference between the two shapes after one hour of treatment. The above data was analyzed statistically using a paired t-test analysis to confirm the validity of this observation. While the results indicate that for the first half hour, there was no significant difference between the pressed-bean mint and the prior art bean-shaped mint in mouth freshening efficacy, the pressed-bean mint was significantly better than the prior art mint from one hour after treatment and onward. The average mint melt times for both products was 4 minutes and 56 seconds.

Figure 9A:
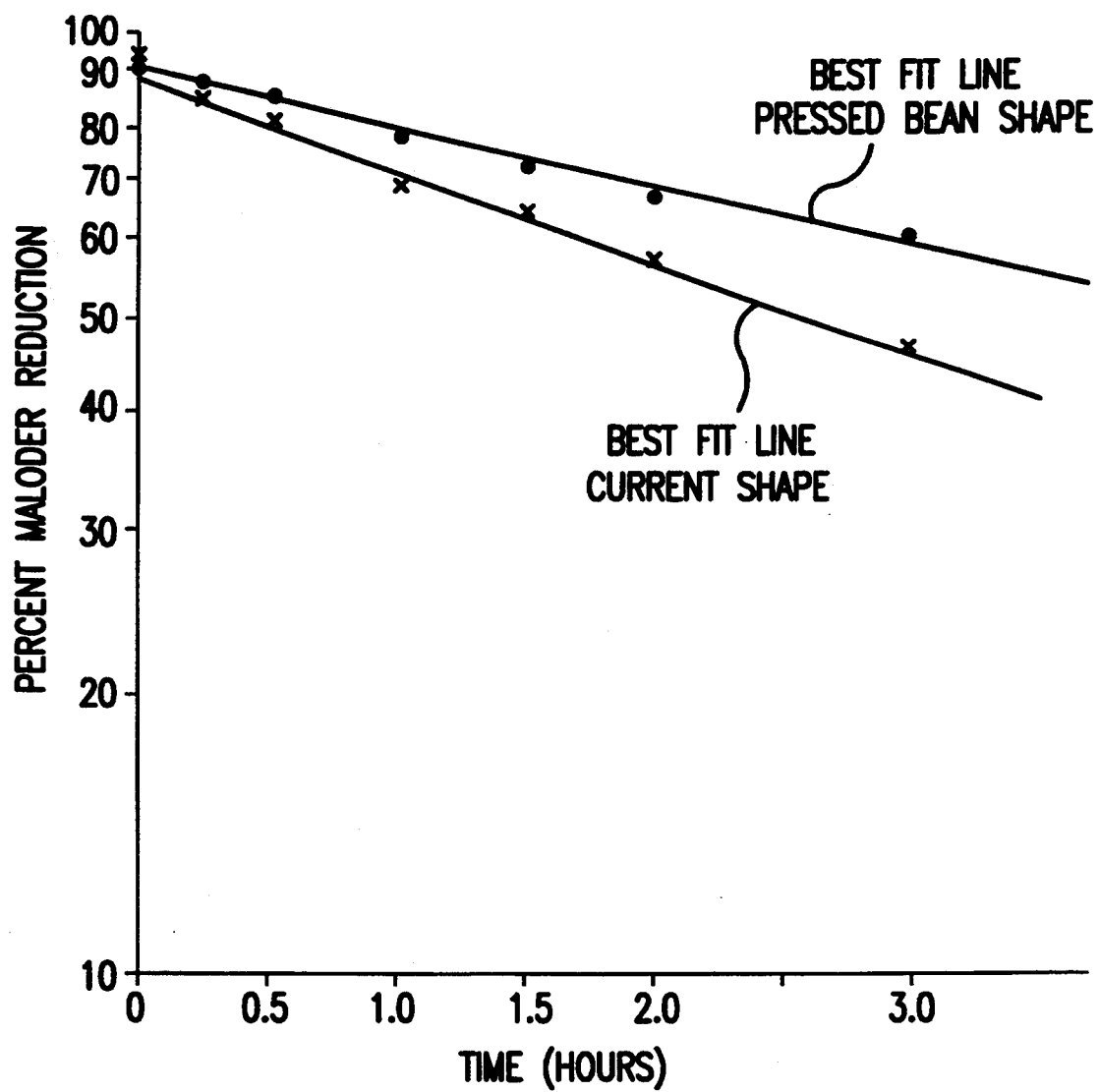
FIGS. 9a–9e are graphs plotting the percent of malodor reduction which various flavors of the invention and prior art mints impart versus the amount of time that has elapsed since the mints were consumed. The graphs in FIGS. 9a–e plot results for mints flavored with, respectively, freshmint, spearmint, wintergreen, orange and cinnamon.
Figure 9B:
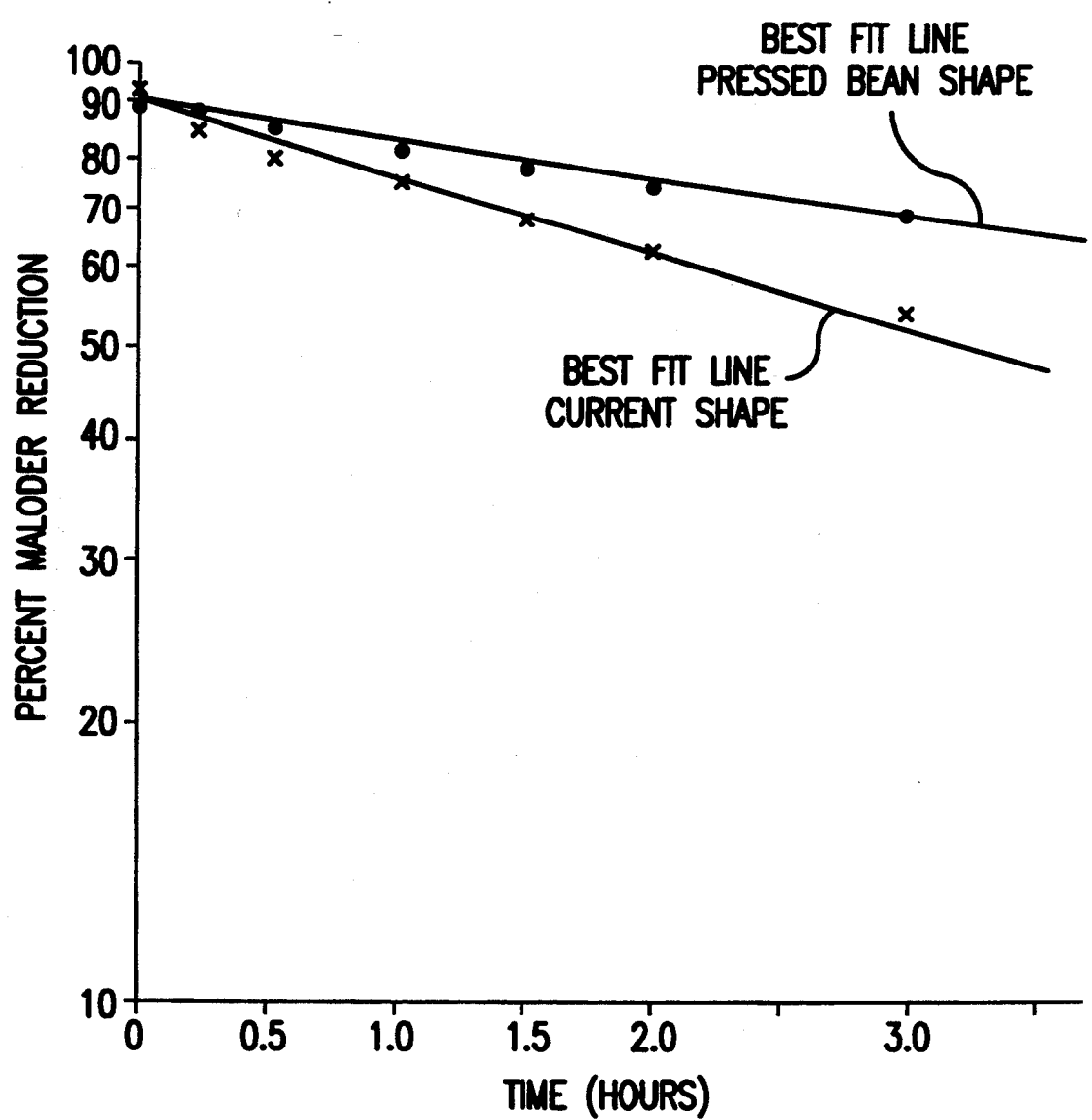

The results generated from the Freshmint mints are plotted in the graph illustrated in FIG. 9a. The equations describing the best fit line for the data illustrated in FIG. 9a were determined as follows:

$$\textit{prior art mint} - Y = 87.1 \times 10^{-0.094t}$$

$$\textit{pressed-bean mint} - Y = 89.7 \times 10^{-0.056\ t}$$

Example 2

| PERCENT MORNING BREATH MALODOR REDUCTION SPEARMINT PRIOR ART MINT VERSUS PRESSED-BEAN MINT | | |
|---|---|---|
| Time (hours) | Prior Art | Pressed-Bean |
| 0.0 | 92.2 | 89.9 |
| 0.25 | 83.1* (t = 3.29) | 87.4 |
| 0.5 | 79.6* (t = 4.85) | 84.5 |
| 1.0 | 73.0* (t = 3.74) | 80.3 |
| 1.5 | 66.0* (t = 10.12) | 77.0 |
| 2.0 | 60.8* (t = 6.67) | 73.1 |
| 3.0 | 53.9* (t = 7.65) | 68.0 |

*Significantly different from pressed-bean mint using paired t-test analysis at 99% and above confidence level.

The results above indicate that immediately after treatment there was no significant difference between the two shapes of spearmint mints in mouth freshening efficacy. Fifteen minutes after treatment and onward, however, the pressed-bean mint according to this invention was significantly (at the 99% confidence level or higher) more efficacious at reducing breath odor than the prior art bean shaped mint. A paired t-test analysis was conducted to confirm the validity of these results. The average melt time for the prior art mint was 5 minutes and 29 seconds. The average melt time for the pressed-bean mint was 4 minutes and 47 seconds. The results generated for the spearmint mints are plotted in the graph illustrated in FIG. 9b. Equations describing the best fit line illustrated in FIG. 9b were determined as follows:

$$\textit{prior art mint} - Y = 88.5 \times 10^{-0.078\ t}$$

$$\textit{pressed-bean mint} - Y = 88.9 \times 10^{-0.040t}$$

Example 3

| PERCENT MORNING BREATH MALODOR REDUCTION WINTERGREEN PRIOR ART MINT VERSUS PRESSED-BEAN MINT | | |
|---|---|---|
| Time (hours) | Prior Art | Pressed-Bean |
| 0.0 | 91.2 | 89.9 |
| 0.25 | 82.8 | 87.1 |
| 0.5 | 76.2* (t = 5.10) | 86.2 |
| 1.0 | 66.3* (t = 14.00) | 83.9 |
| 1.5 | 57.1* (t = 13.27) | 78.0 |
| 2.0 | 53.1* (t = 9.16) | 72.0 |

PERCENT MORNING BREATH MALODOR REDUCTION WINTERGREEN PRIOR ART MINT VERSUS PRESSED-BEAN MINT

| Time (hours) | Prior Art | Pressed-Bean |
|---|---|---|
| 3.0 | 51.8* (t = 10.33) | 68.3 |

*Significantly different from pressed-bean mint using paired t-test analysis at 99% and above confidence level.

The above data suggests a significant difference between the two shapes after residence in the subjects' mouth. To test the validity of this observation, the data was analyzed statistically using a paired t-test analysis. The data and statistical analysis indicate that immediately after treatment there was no significant difference between the two shapes of wintergreen flavored mints in mouth freshening efficacy. Thirty minutes after treatment and onward, however, the pressed-bean mint was significantly (at the 99% confidence level or higher) more efficacious in reducing breath odor than the prior art bean-shaped mint. The average mint melt time for the products were as follows:

*prior art mint*—5 minutes, 3 seconds

*pressed-bean mint*—4 minutes, 13 seconds.

Figure 9C:
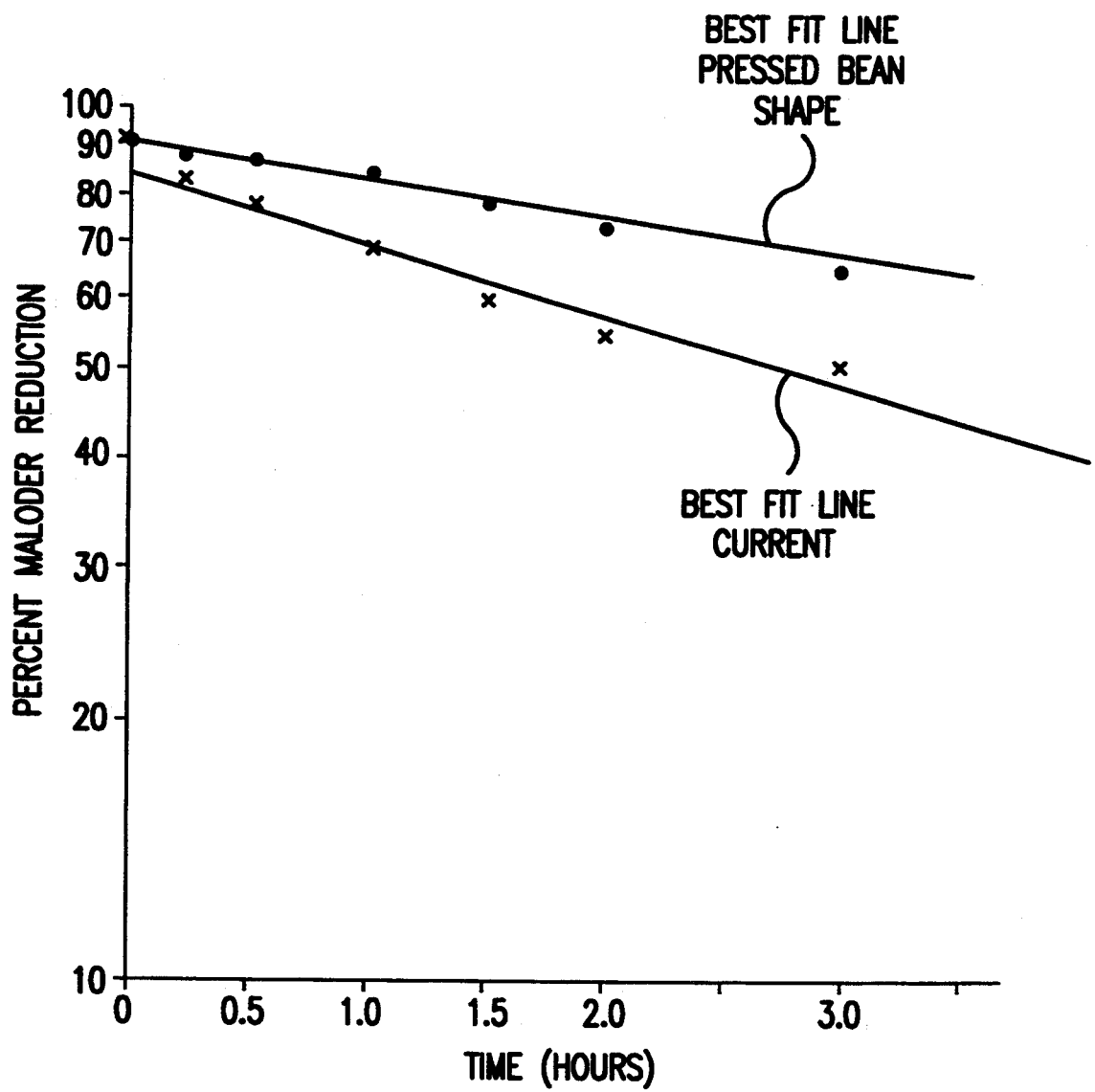

The results generated for the wintergreen mints are plotted in the graph illustrated in FIG. 9c. Equations describing the best fit line illustrated in FIG. 9c were determined as follows:

*prior art mint*—$Y=83.6\times 10^{-0.082t}$

*pressed-bean mint*—$Y=89.5\times 10^{-0.040t}$

Example 4

PERCENT MORNING BREATH MALODOR REDUCTION ORANGE PRIOR ART MINT VERSUS PRESSED-BEAN MINT

| Time (hours) | Prior Art | Pressed-Bean |
|---|---|---|
| 0.0 | 88.3 | 89.9 |
| 0.25 | 87.1 | 89.2 |
| 0.5 | 86.8 | 88.0 |
| 1.0 | 79.3* (t = 3.32) | 85.0 |
| 1.5 | 76.4* (t = 4.26) | 82.8 |
| 2.0 | 73.7** (t = 2.09) | 77.5 |
| 3.0 | 64.6*** (t = 1.74) | 68.0 |

*Significantly different from pressed-bean mint using paired t-test analysis at 99% and above confidence level.
**Significantly different from pressed-bean mint using paired t-test at the 95% confidence level.
***Significantly different from pressed-bean mint using paired t-test at the 90% confidence level.

The above data suggests a significant difference between the two shapes after residence in the test subjects' mouths. To test the validity of this observation the above data was analyzed statistically using a paired t-test analysis. The data and statistical analysis indicate that immediately after treatment, the two shapes of orange mints were equally efficacious in reducing breath odor. One hour after treatment and onward, however, the pressed-bean mint was significantly (at the 90% confidence level or higher) more efficacious in reducing the breath odor than the prior art bean-shaped mint. Average mint melt time for the prior art bean shaped mint was 4 minutes and 3 seconds. Average mint melt time for the pressed-bean mint was 4 minutes.

Figure 9D:
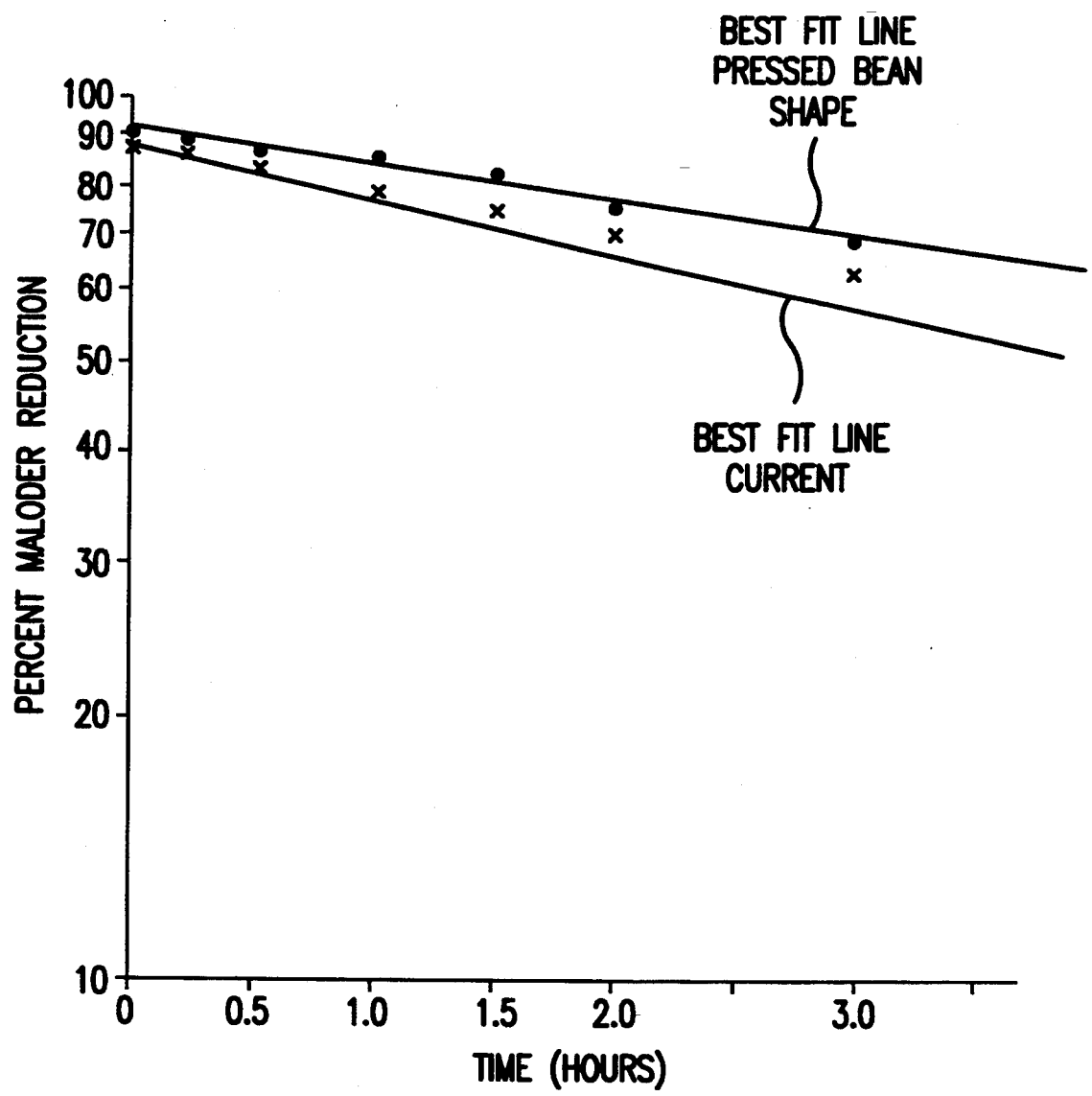

The results generated for the orange mints are plotted in the graph illustrated in FIG. 9d. Equations describing the best fit line illustrated in FIG. 9d were determined as follows:

*prior art mint*—$Y=88.5\times 10^{-0.045t}$

*pressed-bean mint*—$Y=92.0\times 10^{-0.040t}$

Example 5

PERCENT MORNING BREATH MALODOR REDUCTION CINNAMON PRIOR ART MINT VERSUS PRESSED-BEAN MINT

| Time (hours) | Prior Art | Pressed-Bean |
|---|---|---|
| 0.0 | 96.7 | 94.8 |
| 0.25 | 89.0* (t = 3.16) | 94.4 |
| 0.5 | 87.2 | 89.9 |
| 1.0 | 81.5** (t = 2.00) | 84.4 |
| 1.5 | 77.4 | 78.2 |
| 2.0 | 70.7 | 72.9 |
| 3.0 | 61.6** (t = 1.83) | 65.1 |

*Significantly different from pressed-bean mint using paired t-test analysis at 99% and above confidence level.
**Significantly different from pressed-bean mint using paired t-test at the 90% confidence level.

The above data was analyzed statistically using a paired t-test analysis in order to test for significant differences between the two shapes of cinnamon mints. The data and statistical analysis indicate that at certain intervals after treatment significant differences in efficacy were achieved. At other intervals after treatment it appears that both products were equally effective in reducing breath odor. It is believed that these results are probably due to the high efficacy of the cinnamon flavor when compared to the other flavors used to prepare the mints. The average mint melt time for the prior art bean-shaped mint was 4 minutes, 50 seconds. The average mint melt time for the pressed-bean mint was 5 minutes.

Figure 9E:
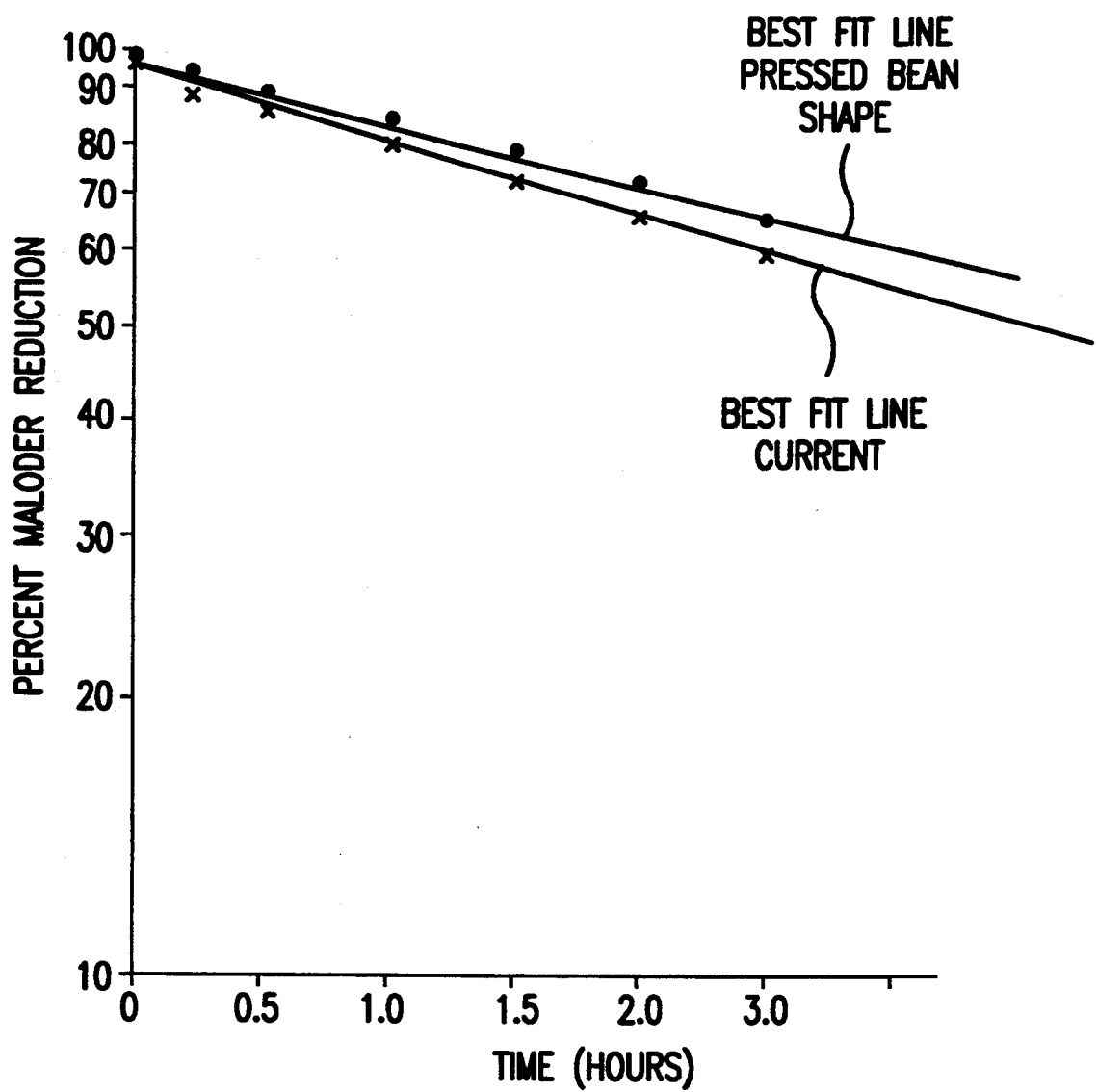

The results generated for the cinnamon mints are plotted in the graph illustrated in FIG. 9e. Equations describing the best fit line illustrated in FIG. 9e were determined as follows:

*prior art bean mint*—$Y=95.3\times 10^{-0.065t}$

*pressed-bean mint*—$Y=95.3\times 10^{-0.054}$

The results in the Examples above indicate that for most flavors, the pressed-bean shape according to this invention significantly improved breath freshening efficacy of the mint over the prior art bean shape. This improvement appears to reside solely in the shape of the mint. The parameters of each mint were absolutely identical in terms of formula, dose, weight, and the production process used. The products compared in the study were also prepared contemporaneously in the same pan coater. Without being held to any particular type of theory, it is believed, that changing the configuration of the mint to that of the invention creates a surface area and shape which facilitates a more uniform distribution of the breach freshening ingredients in the mouth. In particular, the new tablet appears to provide the necessary additional surface area so that the number of taste buds in the mouth that come in contact with the tablet is sufficiently increased to provide a significant improvement in the tablet's breath freshening efficacy.

This improvement is significant not only in the fact that the pressed-bean mint is more efficacious than the prior art mint, but also in the fact that the improvement is obtained using the same amount of essence or flavoring and mint, i.e., the same amount of breath freshening ingredients.

Since many modifications, variations and changes in detail may be made to the described embodiments, it is intended that all matter in the foregoing description and shown in the accompanying drawings be interpreted as illustrative and not in a limiting sense.

What is claimed is:

1. A tablet comprising a tablet body containing a natural and/or artificial flavorant, the tablet including oblong front and back portions having opposing ends connected by substantially parallel sides, the tablet being substantially elliptical when viewed end-on, the tablet having a thickness dimension front-to-back, a width dimension side-to-side, and a length dimension end-to-end, wherein the length dimension and the width dimension have a ratio in the range of about 1.28:1 to about 1.93:1 and the width dimension and the thickness dimension have a ratio in the range of about 1.08:1 to about 2.25:1.

2. A tablet in accordance with claim 1 having a weight within the range of about 0.25 g to 0.5 g.

3. A tablet in accordance with claim 1 wherein said thickness dimension is within the range of from about 4.5 mm to about 6.0 mm, said width dimension is within the range of from about 7.5 mm to about 8.5 mm, and said length dimension is within the range of from about 12 mm to about 13 mm.

4. A tablet in accordance with claim 3 having a weight within the range of about 0.3 g to 0.45 g.

5. A tablet in accordance with claim 1 wherein said thickness dimension is within the range of from about 5 mm to about 5.6 mm, said width dimension is within the range of from about 7.7 mm to about 8.3 mm, and said length dimension is within the range of from about 12.3 mm to about 12.9 mm.

6. A tablet in accordance with claim 5 having a weight within the range of about 0.33 g to 0.43 g.

7. A tablet in accordance with claim 1 wherein said thickness dimension is within the range of from about 5.1 mm to about 5.5 mm, said width dimension is within the range of from about 7.8 mm to about 8.2 mm, and said length dimension is within the range of from about 12.4 mm to about 12.8 mm.

8. A tablet in accordance with claim 7 having a weight within the range of about 0.34 g to 0.42 g.

9. A tablet in accordance with claim 1 wherein said thickness dimension is within the range of from about 5.2 mm to about 5.4 mm, said width dimension is within the range of from about 7.9 mm to about 8.1 mm, and said length dimension is within the range of from about 12.5 mm to about 12.7 mm.

10. A tablet in accordance with claim 9 having a weight within the range of about 0.35 g to 0.41 g.

11. A tablet in accordance with claim 1 wherein said thickness dimension is about 5.3 mm, said width dimension is about 8.0 mm, and said length dimension is about 12.6 mm.

12. A tablet in accordance with claim 11 having a weight within the range of about 0.36 g to 0.4 g.

13. A tablet in accordance with claim 1 wherein the opposing ends of the tablet body's oblong front and back face portions are semi-circular.

14. A tablet in accordance with claim 1 having a weight within the range of about 1.0 g to about 2.0 g.

15. A tablet in accordance with claim 1 wherein the opposing ends of the tablet's oblong front and back portions are semi-circular and have a radius of curvature such that the ratio of the radius of curvature and the thickness dimension of the tablet body is in the range of about 1.20:1 to about 1.40:1.

16. A tablet in accordance with claim 1 wherein the opposing ends of the tablet's oblong front and back portions are semicircular and have a radius of curvature such that the radius of curvature is equal to about one half of the tablet body's width.

* * * * *

UNITED STATES PATENT AND TRADEMARK OFFICE
CERTIFICATE OF CORRECTION

PATENT NO. : 5,431,918
DATED : July 11, 1995
INVENTOR(S) : Pietro Ferrero et al.

It is certified that error appears in the above-indentified patent and that said Letters Patent is hereby corrected as shown below:

Col. 8, line 49, "*pressed-bean mint* - $Y = 95.3 \times 10^{-0.054}$" should be -- *pressed-bean mint* - $Y = 95.3 \times 10^{-0.054t}$ --.

Signed and Sealed this

Twentieth Day of February, 1996

Attest:

BRUCE LEHMAN

*Attesting Officer*   *Commissioner of Patents and Trademarks*